US006777234B1

(12) United States Patent
Dennis et al.

(10) Patent No.: US 6,777,234 B1
(45) Date of Patent: Aug. 17, 2004

(54) MAMMALIAN MUSCLE CONSTRUCT AND METHOD FOR PRODUCING SAME

(75) Inventors: Robert G. Dennis, Ann Arbor, MI (US); Paul Kosnik, Bay City, MI (US); William M. Kuzon, Jr., Ann Arbor, MI (US); John A. Faulkner, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 251 days.

(21) Appl. No.: 09/709,890

(22) Filed: Nov. 9, 2000

Related U.S. Application Data

(62) Division of application No. 09/153,721, filed on Sep. 15, 1998, now Pat. No. 6,207,451.

(51) Int. Cl.[7] .................................................. C12N 5/00

(52) U.S. Cl. ................. 435/395; 435/283.1; 435/305.1; 435/325; 435/402

(58) Field of Search .............................. 435/325, 395, 435/402, 283.1, 305.1

(56) References Cited

U.S. PATENT DOCUMENTS

| | | | |
|---|---|---|---|
| 4,605,623 A | | 8/1986 | Malette et al. |
| 4,940,853 A | | 7/1990 | Vandenburgh |
| 5,153,136 A | | 10/1992 | Vandenburgh |
| 5,443,950 A | | 8/1995 | Naughton et al. |
| 5,618,718 A | | 4/1997 | Auger et al. |
| 5,756,350 A | * | 5/1998 | Lee et al. |
| 6,207,451 B1 | * | 3/2001 | Dennis et al. |

OTHER PUBLICATIONS

Herman A. Vandenburgh Et Al., Skeletal Muscle Growth is Stimulated by Intermittent Stretch–Relaction In Tissue Culture, The American Physiological Society, 1989, pp. C674–C682.

Herman A. Vandenburgh, A Computerized Mechanical Cell Stimulator for Tissue Culture: Effects on Skeletal Muscle Organogenesis, In Vitro Cellular & Developmental Biology, vol. 24, No. 7, Jul., 1988, pp. 609–619.

Herman A. Vandenburgh Et Al., Longitudinal Growth of Skeletal Myotubes in Vitro in a New Horizontal Mechanical Cell Stimulator, In Vitro Cellular & Developmental Biology, vol. 25, No. 7, Jul., 1989, pp. 607–616.

Shansky Et Al., Letter to the Editor: A Simplified Method for Tissue Engineering Skeletal Muscle Organoids In Vitro, In Vitro Cell. Dev. Biol., Oct., 1997, pp. 659–661.

(List continued on next page.)

*Primary Examiner*—Leon B. Lankford, Jr.
(74) *Attorney, Agent, or Firm*—Brooks & Kushman P.C.

(57) ABSTRACT

A mammalian muscle construct and a method for producing the construct are provided. The mammalian muscle construct includes a substrate and a plurality of separate anchors secured to the substrate. Myogenic precursor cells are provided on the substrate with at least some of the cells in contact with the anchors. The myogenic precursor cells are cultured in vitro under conditions to allow the cells to become confluent between the anchors. The anchors are receptive to the cells and allow the cells to attach thereto, such that placement of the anchors controls the size and shape of the muscle construct formed. Specifically, the anchors include separate fragments of biocompatible material secured to the substrate, wherein cell adhesion molecules are associated with each fragment to facilitate attachment of the precursor cells to the fragment.

23 Claims, 4 Drawing Sheets

(1 of 4 Drawing Sheet(s) Filed in Color)

OTHER PUBLICATIONS

Herman A. Vandenburgh Et Al., Computer–Aided Mechanogenesis of Skeletal Muscle Organs from Single Cells in Vitro, The FASEB Journal, vol. 5, Oct. 1991, pp. 2860–2867.

Herman A. Vandenburgh Et Al., Brief Report: Tissue–Engineered Skeletal Muscle Organoids for Reversible Gene Therapy, Human Gene Therapy (Nov. 10, 1996), pp. 2195–2200.

* cited by examiner

MAMMALIAN MUSCLE CONSTRUCT AND METHOD FOR PRODUCING SAME

This application is a divisional of U.S. application Ser. No. 09/153,721 filed on Sep. 15, 1998, now U.S. Pat. No. 6,207,451.

TECHNICAL FIELD

This invention relates to the field of tissue engineering, and more particularly to a mammalian muscle construct and a method for producing the construct in vitro.

BACKGROUND ART

At present, three-dimensional tissues are capable of being produced in vitro using various types of cells. For example, U.S. Pat. No. 5,443,950 issued to Naughton et al. describes three-dimensional cultures for bone marrow, skin, liver, vascular, and pancreatic tissues which are grown within synthetic matrices. In these tissues as well as others, investigators have been successful in proliferating cells and tissues in vitro such that the resulting three-dimensional tissues, termed "organoids" or "constructs", display many of the characteristics of their in vivo counterparts. These constructs have a variety of foreseeable applications, ranging from transplantation in vivo to functional and pharmacological testing in vitro.

In terms of muscle tissue, in vitro constructs of smooth muscle, cardiac muscle, and skeletal muscle have each been formulated. For example, U.S. Pat. No. 5,618,718 issued to Auger et al. describes the production of a contractile smooth muscle cell construct, and U.S. Pat. No. 4,605,623 issued to Malette et al. describes a method for cultivating the three-dimensional growth of cardiac myocytes. These smooth muscle and cardiac muscle constructs were each developed using mammalian muscle cells, specifically, human muscle cells.

In contrast, the majority of skeletal muscle organoids have been developed using avian muscle cells. In particular, a series of studies conducted by Vandenburgh and colleagues involved the production of organoids from avian muscle cells grown on an expandable, SILASTIC® membrane (Vandenburgh, *In Vitro Cell. Dev. Biol.* 24: 609–619, 1988; Vandenburgh et al., *Am. J. Physiol.* 256 (*Cell Physiol.* 25): C674–C682, 1989; Vandenburgh et al., *In Vitro Cell. Dev. Biol.* 25: 607–619, 1989; Vandenburgh et al., *FASEB J.* 5: 2860–2867, 1991). Since avian muscle is structurally and functionally distinct from mammalian muscle, organoids developed from avian muscle have no direct clinical application. A few skeletal muscle constructs have been developed using mammalian muscle grown within a synthetic matrix (Vandenburgh et al., *Hum. Gene Ther.* 7: 2195–2200, 1996; Shansky et al., *In Vitro Cell Dev. Biol.* 33: 659–661, 1997). However, the constructs in these studies originated from cells extracted from neonatal rats or immortal cell lines (C2C12) established from C3H mice which, due to their age or pathology, have limited clinical significance.

Previous methods of organoid production have additional drawbacks. First, in the majority of the studies by Vandenburgh and colleagues described above, as well as in U.S. Pat. Nos. 4,940,853 and 5,153,136, both issued to Vandenburgh, mechanical strain is applied to the skeletal muscle organoids for their proper development, such that complex mechanical fixturing and control electronics are required. Second, both the mammalian and avian skeletal muscle constructs have a limited in vitro life span of approximately four weeks, preventing their use for long-term functional or pharmacological studies.

Perhaps the most serious drawback of previous studies involving the growth of three-dimensional tissues is that the type of anchor systems to which the tissues attach restricts the ability to functionally evaluate the tissues. For instance, when a synthetic membrane or matrix is utilized, the contractile function of the organoids may be difficult to determine separate from the matrix material due to the mechanical preloads of the matrix material. When synthetic anchors such as stainless steel pins or mesh are employed, the tissue merely grows around the anchors instead of into them, such that there is a large discontinuity in mechanical impedance. This discontinuity creates a stress concentration, which could lead to cell damage when the tissue contracts.

DISCLOSURE OF THE INVENTION

Therefore, it is an object of the present invention to provide a mammalian muscle construct which is developed in vitro from cells extracted from mammals of any age.

It is another object of the present invention to provide an anchor system for forming a mammalian muscle construct wherein the anchor system does not restrict the ability to functionally evaluate the construct.

It is a further object of the present invention to provide a non-synthetic anchor system for forming a mammalian muscle construct.

It is a further object of the present invention to provide a method for producing mammalian muscle constructs which does not require the application of external mechanical strain.

It is still another object of the present invention to provide a mammalian muscle construct which is capable of being maintained in vitro for longer than four weeks.

Accordingly, a mammalian muscle construct and a method for producing the construct are provided. The mammalian muscle construct includes a substrate and a plurality of separate anchors secured to the substrate. Myogenic precursor cells are provided on the substrate with at least some of the cells in contact with the anchors. The myogenic precursor cells are cultured in vitro under conditions to allow the cells to become confluent between the anchors. The anchors are receptive to the cells and allow the cells to attach thereto, such that placement of the anchors controls the size and shape of the muscle construct formed.

For use in producing the mammalian muscle construct, an anchor system for controllably forming tissue from precursor cells in vitro and a method for making the anchor system are provided. The anchor system includes a substrate and a plurality of separate fragments of biocompatible material secured to the substrate. Cell adhesion molecules are associated with each fragment to facilitate attachment of the precursor cells to the fragment. Therefore, the placement of the fragments on the substrate defines an area for confluence of the cells to control the size and shape of the tissue formed.

The above objects and other objects, features, and advantages of the present invention are more readily understood from a review of the attached drawings and the accompanying specification and claims.

BRIEF DESCRIPTION OF THE DRAWINGS

The file of this patent contains at least one photograph executed in color. Copies of this patent with the color photograph(s) will be provided by the Patent and Trademark Office upon request and payment of the necessary fee.

BEST MODES FOR CARRYING OUT THE INVENTION

Figure 1:
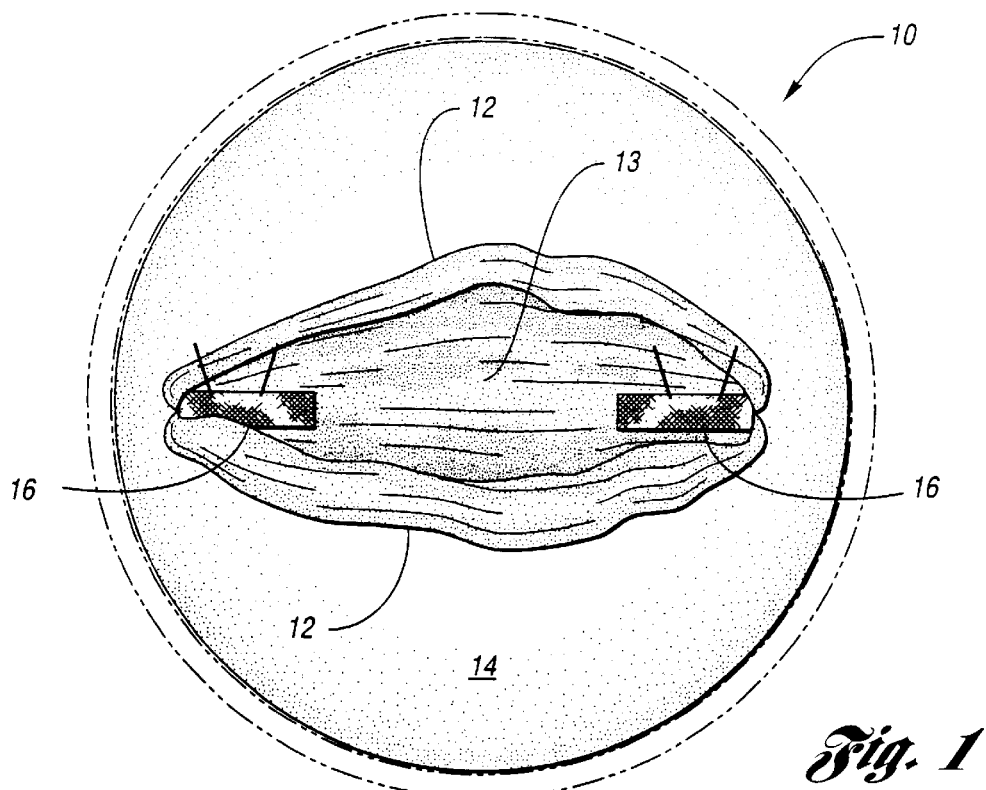
FIG. 1 shows a skeletal muscle construct of the present invention in the process of forming.

The present invention provides a three-dimensional mammalian skeletal muscle construct, or "myooid", and a method for producing the myooid from primary cell culture.

As described herein, precursor cells are defined as any cell which can be used to develop a particular tissue of interest. More specifically, myogenic precursor cells are defined as any cell which can develop into skeletal muscle, smooth muscle, or cardiac muscle tissue. In the case of skeletal muscle tissue, precursors include, but are not limited to, satellite cells and myoblasts. In addition, stem cells, such as bone marrow cells, or fibroblasts can be induced to differentiate into myogenic precursors, as is known in the art.

By way of example, the skeletal muscle construct and method for producing the construct of the present invention are described with reference to the use of muscle tissue originating from rats. However, the construct and method of the present invention are not intended to be limited to one particular cell origin or age, myooid shape, time frame, component concentration, or culture condition. One skilled in the art can readily appreciate that various modifications can be made to the method described herein without departing from the scope of the invention disclosed.

As is apparent to those skilled in the art, the preparation of the anchor materials and the culture of the cells described below must be carried out in accordance with commonly practiced cell culture techniques. For example, all materials and media which will be placed in contact with living cells must be appropriately sterilized and handled. In addition, the cells and myooids must be maintained in an otherwise aseptic environment.

Production of Anchors

The present invention provides anchors to which the myogenic precursor cells attach in vitro for myooid formation. In accordance with the present invention, attachment of the myogenic precursor cells to the anchors does not restrict the ability to perform subsequent functional measurements on the myooids. The anchors comprise fragments of biocompatible material with cell adhesion molecules associated therewith, wherein the anchors are permeable to allow the ingrowth of tissue. Although the anchor system and method of the present invention is described herein with reference to the production of skeletal muscle in vitro, use of the anchor system in the formation of other tissue constructs may be possible.

Acellularized Muscle Anchors. In a first embodiment of the present invention, the anchors are produced from small acellularized fragments of skeletal muscle, wherein the acellularized fragments contain ECM attachment molecules, such as laminin, collagen, and pronectin. Advantageously, the muscle fragments for producing the anchors need not originate from the same species as the muscle cells used to generate the myooid. For example, anchors produced from mouse muscle may be used to produce myooids from rat myogenic precursor cells.

To produce the acellularized muscle anchors of the present invention, culture dishes are first prepared by mixing and pouring SYLGARD® into the dishes to form a substrate. The SYLGARD® is allowed to dry and harden for at least two weeks prior to use of the dishes to allow the toxic byproducts of room temperature vulcanization to evolve and dissipate. Next, under general anesthesia, whole rat muscles are surgically removed. For example, due to ease of dissection, hindlimb muscles such as the soleus, extensor digitorum longus, or tibialis anterior are often utilized. After the muscles have been removed, they are placed in phosphate-buffered saline (PBS) and cut into strips preferably no more than 3 mm in diameter. The strips are pinned at slack length in the culture dishes, and several dozen muscle strips can be placed in each dish.

The muscle strips are covered with a solution of 80% glycerol and 20% saline by volume with 7 g/L EDTA and 0.5 g/L $NaN_3$ in order to disrupt the cell membrane, and allowed to sit in covered dishes at room temperature for approximately 48 hours. $NaN_3$ is used in the above solutions and other solutions as a preservative. Next, the dishes are drained, flushed with water, and re-filled with fresh 80% glycerol solution, then allowed to sit for approximately 24 hours. Then, the dishes are drained, flushed with water, and refilled with a solution of 3% deoxycholic acid (sodium salt) and 0.05% $NaN_3$ in distilled water in order to begin intracellular protein dissociation, then allowed to sit for an additional 24 hours. The dishes are then drained, flushed with water, and refilled with fresh glycerol solution in order to complete the removal of lipid-soluble cell structures. After approximately 48 hours, the glycerol solution is drained and replaced with fresh glycerol solution and the dishes are allowed to sit for 24 hours.

Then, for additional cellular protein denaturing, the dishes are flushed with water and refilled with a solution of 1% SDS and 0.05% $NaN_3$ in distilled water. After 24 to 48 hours, the dishes are rinsed in water and refilled with a solution of 3% TRITON® X-100 (Sigma T-9284) and 0.05% $NaN_3$ in distilled water in order to remove denatured proteins from the extracellular matrix. After an additional 24 to 48 hours, the dishes are rinsed in water and refilled with the SDS solution for final protein denaturing and removal, and allowed to sit for approximately 24 to 48 hours. The dishes are then thoroughly rinsed in water, and refilled with a solution of 0.05% $NaN_3$ in 0.9% saline in which the acellularized muscle fragments will remain until their use. The acellularized muscle fragments are now stored, at room temperature, pinned in the culture dishes, and will remain usable for at least 6 months. Prior to use, the fragments are preferably cut into 2 mm cubes.

Laminin-coated suture anchors. In an alternative embodiment of the present invention, silk suture segments coated with cell adhesion molecules are utilized as anchors. Preferably, the cell adhesion molecules are extracellular matrix (ECM) attachment molecules, most preferably laminin. These alternative anchors simplify the process of myooid production by eliminating the need to sacrifice animals for the production of acellularized muscle fragments. In addition, compared with the acellularized anchors, the synthetic anchors are easier to attach to instrumentation used for subsequent measurements of myooid contractile function. The synthetic anchors are produced by cutting silk suture, preferably size 0, to a convenient length. Lengths of 6 to 8 mm are easily pinned in place, but the length can be varied without limit as dictated by the specific circumstances. The segments of suture are dipped in a solution of 50 µg of laminin, such as natural mouse laminin (Gibco), in 1 ml PBS (pH 7.2), with care taken to thoroughly wet the suture. The suture segments are then allowed to dry overnight before use.

Preparation of Media

In accordance with the present invention, media are preferably prepared in the following manner for myooid production. Stock growth medium (GM) is prepared with the following constituents: 400 ml filter sterilized F12 nutrient medium (Ham), 100 ml fetal bovine serum, and 100 u/ml Penicillin G.

Stock differentiation medium (DM) is prepared with the following constituents: 465 ml DMEM, 35 ml horse serum, and 100 u/ml Penicillin G. Tissue dissociation medium (D&C) is prepared as a solution of DMEM with 5% by weight dispase and 0.5% by weight collagenase type IV. The D&C medium is prepared and filter-sterilized immediately prior to use, as stock solutions cannot be maintained.

In addition to the above solutions, a stock preincubation medium (PI) is also prepared using 90 ml DM and 10 ml of a solution of 0.05% $NaN_3$ in 0.9% saline, which should subsequently be filter-sterilized. As will be described below, PI medium is used to activate myogenic precursor cells, specifically satellite cells, in adult and aged animals before complete tissue dissociation.

Preparation of Culture Dishes

For the production of each myooid, an individual culture dish (35 mm diameter) is coated with SYLGARD® as described above. For myooid formation, the SYLGARD® substrate may be coated with cell adhesion molecules, such as ECM attachment molecules. As an alternative or in addition to the ECM coating, the culture dish should be preincubated in a serum-containing media, such as GM. Pre-soaking the culture dishes with serum-containing media for about four days prior to seeding with myogenic precursor cells has the effect of soaking out toxins from the substrate and anchors.

In a preferred embodiment, the SYLGARD® substrate is coated with both serum-containing media and ECM molecules, specifically laminin. The laminin concentration on the substrate is used to control both the rate of cell growth and the time of cell monolayer delamination for the formation of the myooid. In particular, the laminin disappears from the substrate within a couple of weeks, which facilitates the detachment process to allow myooid formation. Higher laminin concentrations result in more rapid formation of dense monolayers of confluent cells, but also delay the delamination of the monolayer. Laminin densities of about 0.3 to 1.5 $\mu g/cm^2$ have been shown to be effective, whereas higher densities may prevent myooid formation. Optimal values for use in the present invention appear to be in the range of about 0.5 to 1.0 $\mu g/cm^2$.

Next, a pair of anchors, either the acellularized muscle anchors or the laminin-coated suture anchors, are pinned into each prepared culture dish. Preferably, the anchors are spaced 10 to 20 mm apart at their closest points. The dishes are then filled with 2.5 ml GM, covered, and sterilized by exposure to ultraviolet light from a germicidal lamp for about 40 minutes. The dishes are maintained at 37° C. in a water-saturated atmosphere containing 5% $CO_2$ for one week prior to seeding with muscle cells in order to pre-soak the anchors. This process removes toxins and allows deposition of cell adhesion proteins from the serum in the media. Although two anchors are used to create the preferred myooid shape of the present invention, more anchors may be used to form any desired size or shape of the construct.

Harvesting of Myogenic Precursor Cells

In accordance with the present invention, myogenic precursor cells, such as satellite cells, may be harvested from neonatal, adult, or aged mammals.

Neonatal Tissue. To harvest cells from neonatal rat tissue, pups from a litter of neonatal rats are anesthetized by placement on ice for approximately 1 hour. After removal of the paws and skin, all muscle tissue from all four limbs is harvested and placed in a culture dish (65 mm diameter) with 8 ml of calcium-free PBS. Muscles are removed under sterile conditions in a Class IIA/B3 biological safety cabinet. All harvested tissue is transferred to a 50 ml conical tube containing 12 ml of D&C solution and stirred for approximately one hour in order to dissociate the tissue. The tube is then centrifuged at 1200 G for approximately 15 minutes. After removal of the supernatant, cells are resuspended in 20 ml of Ham's F12 with 20 mg of collagenase type IV and incubated at 37° C. for one hour to allow tissue dissociation. The tube is again centrifuged at 1200 G for 15 minutes, after which the supernatant is removed and the cells are resuspended in GM. Within this cell suspension will likely be fibroblasts in addition to the myogenic precursor cells. There is not a need to eliminate the fibroblasts before culturing the myogenic precursor cells, and the inclusion of fibroblasts may even facilitate the generation of ECM materials in the construct.

Adult or Aged Tissue. Alternatively, adult or aged rats are placed under general anesthesia, and skeletal muscles are harvested therefrom and cut into strips. Unlike the neonatal tissue, muscle tissue from adult or aged animals will yield more satellite cells if initially preincubated before complete tissue dissociation. The increased activation of satellite cells likely results from the use of $NaN_3$ in the PI medium which may signal, without actually causing, imminent cell death.

To preincubate the muscle tissue, the strips are pinned in a SYLGARD® coated culture dish (35 mm diameter), covered with 2.5 ml of PI, and sterilized by exposure to ultraviolet light for approximately 40 minutes. The dishes are then maintained at 37° C. in a water-saturated atmosphere containing 5% $CO_2$ for 24 to 72 hours, where optimal pre-incubation times may vary for different muscles. For example, in the case of rat extensor digitorum longus, soleus, and tibialis anterior muscles, the muscles are cut into strips no larger than 3 mm in diameter, then pre-incubated for 40 to 60 hours.

After pre-incubation, each muscle strip is placed into a 50 ml conical tube with 15 ml D&C solution and incubated in a shaker bath at 37° C. for approximately 3 hours until complete dissociation is observed. Immediately upon complete tissue dissociation, the tubes are centrifuged at 1200 G for 15 minutes. Subsequently, the supernatant is aspirated and cells are reconstituted with 5 ml GM. As with the cells derived from neonatal tissue, fibroblasts may be included in the cell suspension.

Myooid Formation

The resuspended myogenic precursor cells derived from neonatal muscle tissue or from adult or aged muscle tissue are plated onto the anchor-prepared dishes described above for myooid formation. Preferably, 2 to 2.5 ml of GM, containing the dissociated tissue from 5 mg to 20 mg of muscle, is transferred to each culture dish. Culture dishes are maintained in a tissue culture incubator at 37° C. in a water-saturated atmosphere of 5% $CO_2$, and are not agitated for at least 24 hours after seeding. Beginning at 48 hours after seeding, GM is replaced every 48 hours until the cells become confluent, which typically requires 3 to 10 days. When cells have reached confluence, additional feedings are made with DM, which is also changed every 48 hours. The cells rapidly fuse to form multinucleated myotubes which begin to spontaneously contract within several days of switching to DM.

Figure 2:
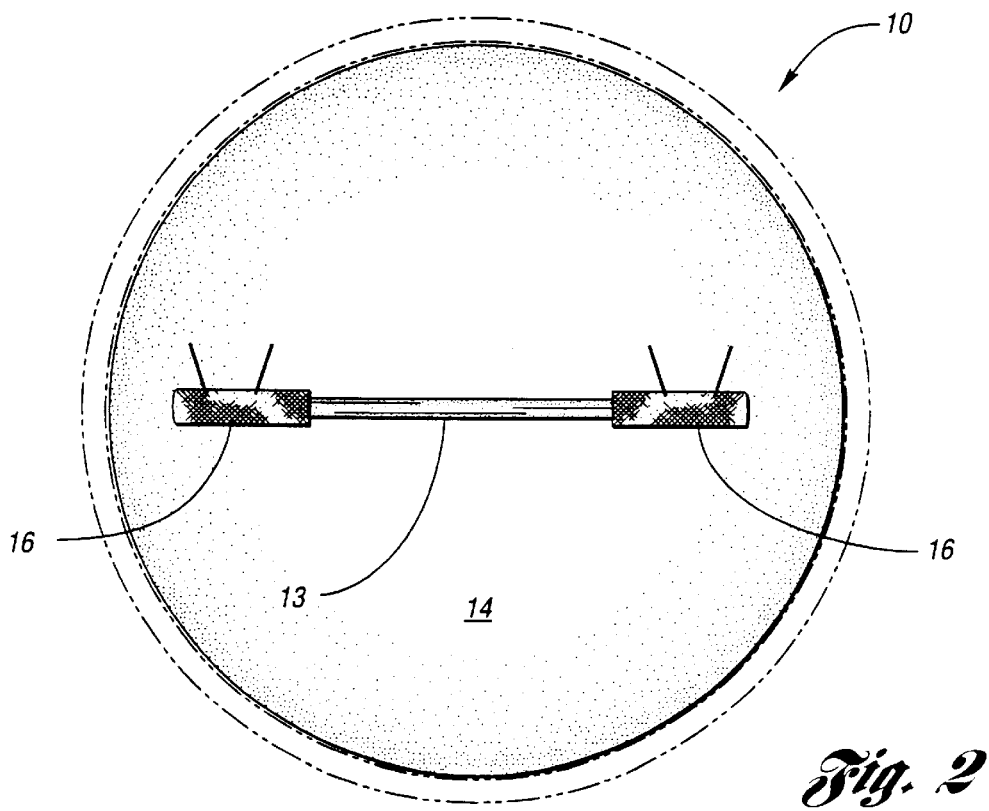
FIG. 2 shows a fully formed skeletal muscle construct in accordance with the present invention.

In accordance with the present invention, the formation of a myooid 10 typically begins with peripheral delamination of the edges 12 of muscle tissue 13 from the substrate 14, as shown in FIG. 1. The delamination process typically commences at 3 to 21 days, corresponding with the disappearance of laminin from the substrate 14, and progresses radially inward until the entire cell monolayer has peeled away from the substrate material 14. The time course of delamination appears to depend upon the plating density, the substrate coating, and the age of the animals from which the cells were extracted. The delamination process is accelerated by spontaneous contraction of the myotubes, which is normal behavior for developing muscle tissue. The delaminating monolayer will eventually roll up and lift off of the substrate to form a cylinder between the two anchors 16, as shown in FIG. 2. For the myooids 10 shown in FIGS. 1 and 2, laminin-coated suture anchors 16 were utilized. When viewed under a microscope, the in-growth of the myooid tissue into the anchor material is apparent.

Figure 3:
FIG. 3 is a photomicrograph of a cross-section of a fully formed skeletal muscle construct such as that shown in FIG. 2.

FIG. 3 is a photomicrograph of a cross-section of a fully-formed myooid 10, such as that shown in FIG. 2. As one skilled in the art will readily appreciate, the myooid cross-section shown in FIG. 3 clearly displays a morphology indicative of in vivo skeletal muscle tissue. The large amounts of extracellular material and central nuclei present suggest that extensive remodeling is in progress.

Myooids are maintained in culture by feeding the culture dishes with 2 ml DM every 48 to 96 hours. The myooids will gradually reduce in diameter from as large as 1.2 mm immediately after formation to as small as 60 $\mu$m after 4 to 12 weeks. While maintained in culture, the myooids will spontaneously contract at frequencies of approximately 0.1 to 2 Hz. The total time in culture for the myooids, including the formation period, ranges from 5 to 12 weeks, depending upon such conditions as the density at which the cells are plated, the anchor material and spacing, the frequency of feeding, and the type and density of the substrate cell adhesion molecules, such as laminin. Using the method of the present invention, a single rat soleus muscle with a mass of about 150–200 mg will yield enough cells to make 12 to 48 myooids, depending upon the preparation of the muscle strips for pre-incubation. A litter of rat neonates yields enough cells to make 50 to 100 myooids.

Functional Measurements

Using the method of the present invention, functional measurements such as the contractile force developed by the myooids can be measured directly without interference from the anchor materials. Contractile properties of the myooids is measured by exciting the myooids with a transverse electric field, identical to the configuration commonly used for standard in vitro muscle experiments where pulse trains are applied to excised muscles via parallel-plate electrodes.

Figure 4:
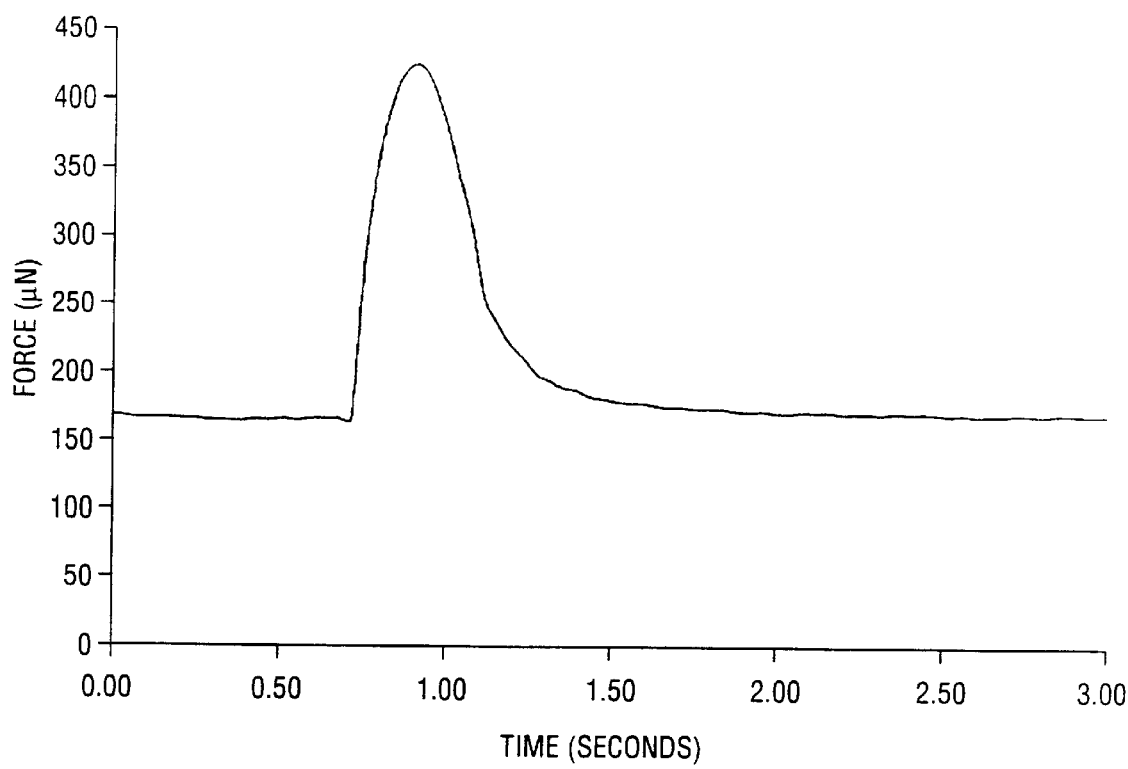
FIG. 4 is a graph showing the elicited twitch force of a skeletal muscle construct of the present invention.
Figure 5:
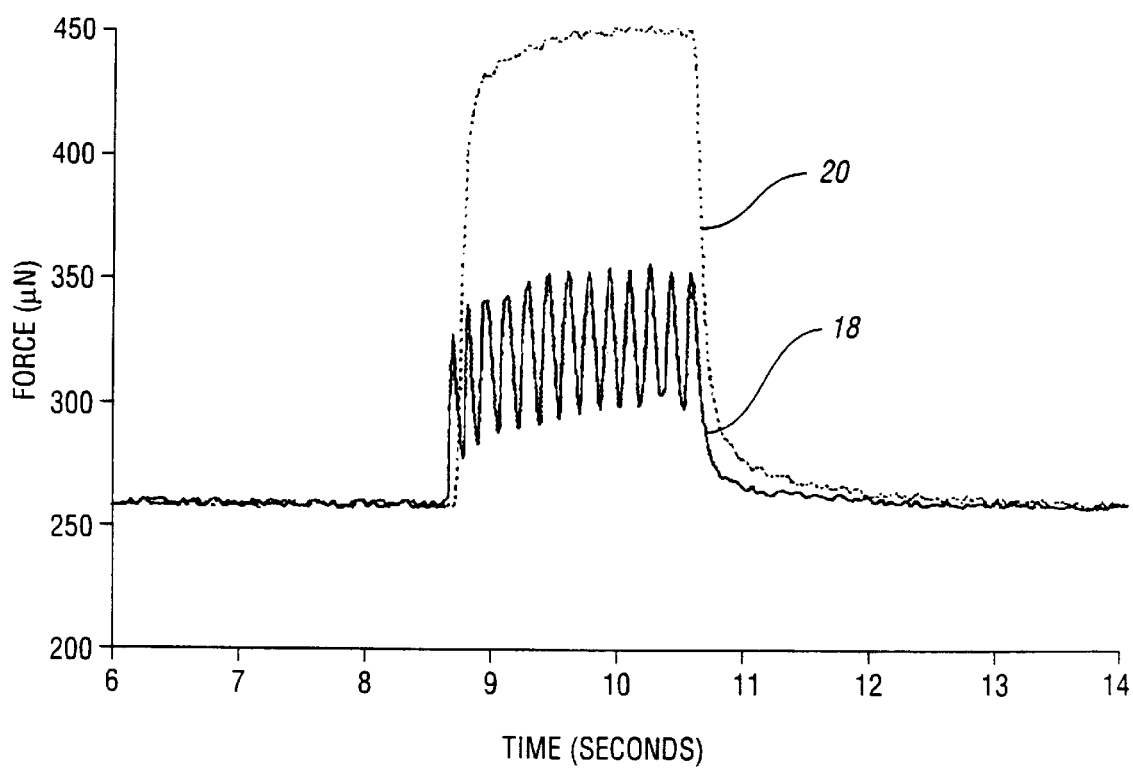
FIG. 5 is a graph depicting the frequency dependence of tetanic fusion for a skeletal muscle construct of the present invention.
Figure 6:
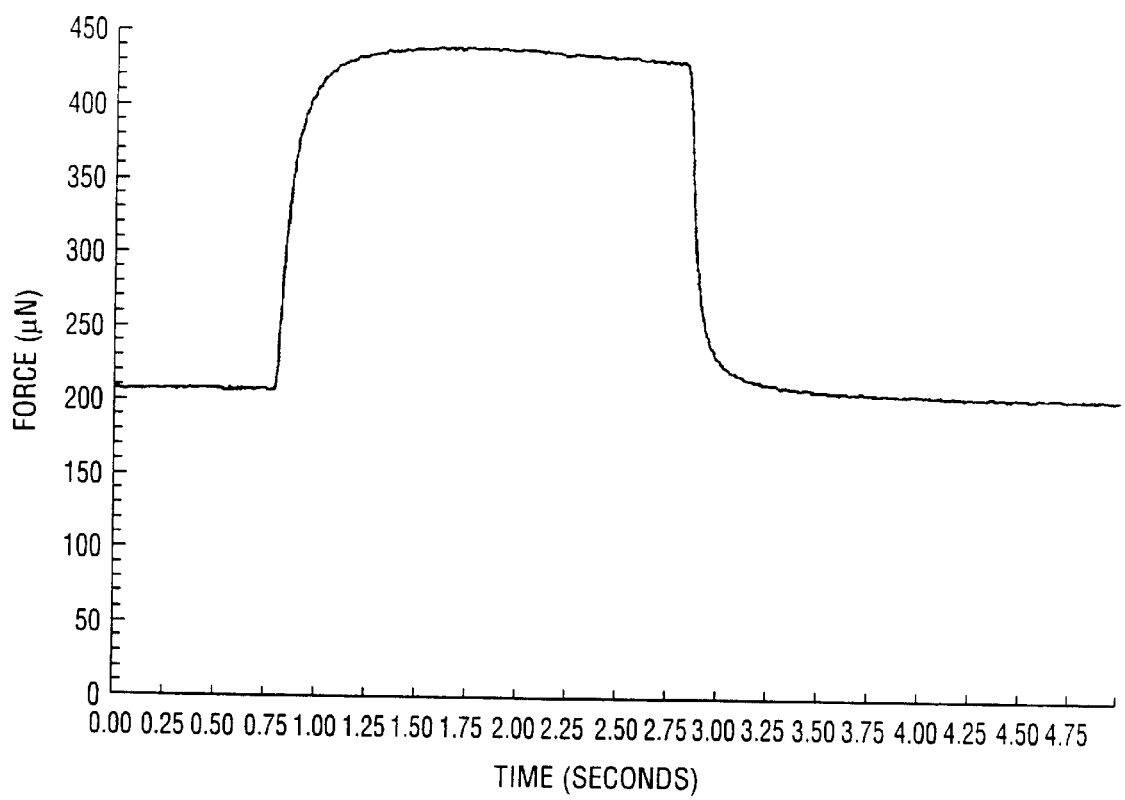
FIG. 6 is a graph of a fused tetanic contraction of a skeletal muscle construct of the present invention.

Referring now to FIGS. 4–6, stimulation pulses were applied via 36 gage platinum electrode wires, spaced approximately 5 mm apart and placed parallel to the myooid on either side thereof. A custom-made optical force transducer, calibrated for forces up to 2 mN with a force resolution of 1 $\mu$N, was used to measure the forces elicited by the electrical excitation. The force transducer arm, constructed from a segment of 27 gage hypodermic tubing, was positioned over the culture dish and tied to one of the pins inserted therein with several small pieces of suture. The pin tied to the transducer arm was then removed from the substrate, while the other end of the myooid remained fixed to the substrate via its pinned anchor. Force transducer voltages for the myooid contractions were recorded using a standard analog-to-digital data acquisition system.

The resulting myooid force traces are readily identifiable to one skilled in the art as being generated by skeletal muscle tissue. In addition, the data for isometric contractile function indicate that the myooid is developmentally arrested in the early stages of myosin isoform expression, as would be expected in the absence of neuronal signals. As shown in FIG. 4, a twitch of the myooid is elicited by a single square pulse. The latency period, time to peak, and half relaxation time, as well as the peak force per cross-sectional area are all within the expected range for skeletal muscle, such as the myooid, that expresses primarily embryonic and/or neonatal myosin isoforms.

In FIG. 5, the effect of stimulation frequency on the fusion of tetanus is clearly evident when 6 Hz stimulation, indicated by reference numeral 18, is compared with 30 Hz stimulation, indicated by reference numeral 20, for the same myooid. The fused tetanic contraction shown in FIG. 6 is also very typical of skeletal muscle in vitro. The ability to generate contractile function and excitability data such as shown in FIGS. 4–6 demonstrates the ability of the myooids of the present invention to be used as an in vitro model of skeletal muscle, allowing the comparison of functional data from the myooids with the extensive pool of data published for mammalian skeletal muscle and muscle fibers in the scientific and clinical literature.

Figure 7:
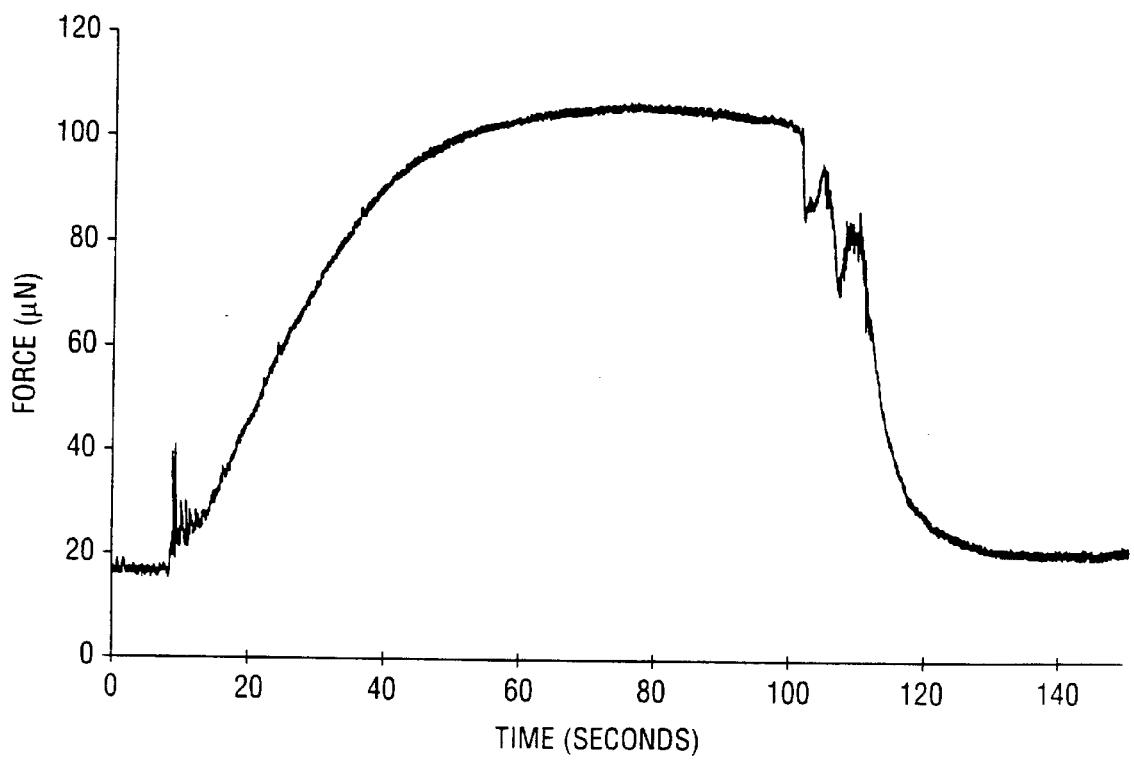
FIG. 7 shows the contractile response of a skeletal muscle construct of the present invention to the addition of caffeine.

FIG. 7 shows the contractile response of a myooid of the present invention to the addition of caffeine. In the graph of FIG. 7, 15 mM of caffeine was added to the culture dish at 8 seconds, then aspirated and replaced with caffeine-free medium at 100 seconds. Note the dramatic response of the myooid to the addition of caffeine, and the immediate relaxation and return to normal passive force levels with the removal of caffeine by replacement of the solution. This indicates that the myooid is not damaged or permanently altered by the addition of large concentrations of caffeine, and that an accurate dose-response curve may be generated. These data suggest that the myooids of the present invention may be useful in evaluating the effects of pharmaceutical agents on muscle function.

Summary

The present invention provides a skeletal muscle construct and a method for producing the construct in vitro from cells extracted from mammals of any age. The construct can be grown to be three-dimensional without the use of a synthetic membrane or matrix. This is accomplished through the use of an anchor system to which the myogenic precursor cells attach, wherein the anchors do not restrict the ability to functionally evaluate the constructs. In addition, the application of external mechanical strain is not required to produce the constructs, and the constructs may be maintained in vitro for up to 12 weeks.

The myooids of the present invention have multiple potential clinical applications including the clinical screening of congenital disease, the commercial testing of the influence of pharmaceuticals or toxic agents on skeletal muscle development and contractile function, the development of tissue engineered skeletal muscle structures for clinical transplantation, and basic scientific research on myogenesis and muscle structure/function relationships. The myooid construct rig may also be useful in validating the effectiveness of gene therapy on human skeletal muscle tissue without requiring the injection of genetic material into human beings.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. An anchor system for controllably forming tissue from precursor cells in vitro, the anchor system comprising:

a substrate;

at least two separate tissue fragments secured to the substrate in spaced relationship; and cell adhesion molecules associated with each fragment which facilitate attachment of the precursor cells to the fragment, wherein the placement of the fragments on the substrate controls the size and shape of the tissue formed.

2. The anchor system of claim 1, wherein the precursor cells include myogenic precursor cells.

3. The anchor system of claim 2, wherein the myogenic precursor cells are harvested from neonatal mammals.

4. The anchor system of claim 2, wherein the myogenic precursor cells are harvested from adult or aged mammals.

5. The anchor system of claim 2, wherein the myogenic precursor cells develop into skeletal muscle tissue.

6. The anchor system of claim 2, wherein the myogenic precursor cells include satellite cells.

7. The anchor system of claim 2, wherein the myogenic precursor cells are derived from stem cells.

8. The anchor system of claim 1, wherein the fragments are permeable to allow the ingrowth of tissue.

9. The anchor system of claim 1, wherein the tissue fragments include acellularized tissue fragments.

10. The anchor system of claim 1, wherein the acellularized muscle fragments and the precursor cells are obtained from different species.

11. The anchor system of claim 1, wherein the substrate is coated with cell adhesion molecules.

12. The anchor system of claim 11, wherein the cell adhesion molecules include laminin.

13. The anchor system of claim 1, wherein the substrate is soaked in serum-containing media.

14. The anchor system of claim 9, wherein the acellularized tissue fragments include acellularized muscle fragments.

15. A method for making an anchor system for controllably forming tissue from precursor cells in vitro, the method comprising:

providing a substrate;

securing at least two separate tissue fragments to the substrate in spaced relationship;

associating cell adhesion molecules with each fragment, wherein the cell adhesion molecules facilitate attachment of the precursor cells to the fragment; and placing the fragments and associated cell adhesion molecules to control the size and shape of the tissue formed.

16. The method of claim 15, wherein the precursor cells include myogenic precursor cells.

17. The method of claim 16, wherein the myogenic precursor cells develop into skeletal muscle tissue.

18. The method of claim 15, wherein the fragments are permeable to allow the ingrowth of tissue.

19. The method of claim 15, wherein the tissue fragments include acellularized tissue fragments.

20. The method of claim 15, further comprising coating the substrate with cell adhesion molecules.

21. The method of claim 20, wherein the cell adhesion molecules include laminin.

22. The method of claim 15, further comprising soaking the substrate in serum-containing media.

23. The method of claim 19, wherein the acellularized tissue fragments include acellularized muscle fragments.

* * * * *